United States Patent [19]

Taylor et al.

[11] Patent Number: 5,654,013

[45] Date of Patent: Aug. 5, 1997

[54] METHOD FOR TREATING ROSACEA

[76] Inventors: Lesli A. Taylor; Ralph L. Bass, both of 820 Churchill, Chapel Hill, N.C. 27514

[21] Appl. No.: 402,896

[22] Filed: Mar. 13, 1995

[51] Int. Cl.$^6$ .................................................. A61K 33/14
[52] U.S. Cl. ............................................. 424/680; 514/859
[58] Field of Search ............................... 424/680; 514/859

[56] References Cited

U.S. PATENT DOCUMENTS

| | | | |
|---|---|---|---|
| 3,574,854 | 4/1971 | Bossard | 424/357 |
| 3,867,522 | 2/1975 | Kligman | 424/153 |
| 4,005,198 | 1/1977 | Skillern | 424/227 |
| 4,443,442 | 4/1984 | Skillern | 424/246 |
| 4,581,226 | 4/1986 | Dillon | 424/49 |
| 5,116,605 | 5/1992 | Alt | 424/70 |
| 5,116,606 | 5/1992 | Alt | 424/70 |
| 5,271,943 | 12/1993 | Bogart et al. | 424/484 |

OTHER PUBLICATIONS

Stern, Canyl "You Don't Have To Live With It", *Parade Magazine*, (Feb. 19, 1995—Sunday), pp. 8 and 10.

Barnhart, Edward R. *Physicians' Desk Reference* (PDR 41 Edition 1987) pp. 1641 and 1642.

Van Nostrand, *Scientific Encyclopedia*, (Copyright, 1938), pp. 548–549.

*Primary Examiner*—Marianne M. Cintins
*Assistant Examiner*—M. Moezie
*Attorney, Agent, or Firm*—Richard E. Jenkins, P.A.

[57] ABSTRACT

A method for the topical treatment of skin affected with acne, rosacea, or a combination thereof. Sodium chloride in a substantially pure form is topically applied to the affected skin by gently gliding the sodium chloride over the affected skin in a manner insufficient to cause abrasion and debridement of the affected skin. A solid block of about 98% to about 100% by weight sodium chloride free of a carrier and/or free of other topical acne-treatment medicaments and/or free of other topical rosacea-treatment medicaments should be used. The applied sodium chloride is left on the skin. Preferably, the affected skin is pre-moistened with water from shaving, bathing, splashing water on the skin, and the like prior to gliding the sodium chloride thereon.

10 Claims, No Drawings

METHOD FOR TREATING ROSACEA

TECHNICAL FIELD

The present invention relates, in general, to a method for the topical treatment of acne and/or rosacea. More particularly, the present invention relates to an improved method for the topical treatment of human skin affected with acne and/or rosacea by gently gliding over the affected skin substantially pure sodium chloride.

RELATED ART

Acne is a skin disorder caused by bacteria that inflames skin glands and hair follicles of humans. Acne typically occurs during the teenage years due to hormonal changes, but occasionally develops as early as the age of nine and sometimes extends well into the age of the mid-twenties. On the other hand, rosacea, which used to be thought of as a type of acne, has more recently been found to be a skin disorder that, in contrast to ache, dilates facial blood vessels in severe cases in humans and typically occurs at the age of about 30 to about 50. It is not known what causes rosacea.

An excellent discussion of the problems of rosacea afflicting those in the 30 to 50 age group can be found in Stern, "You Don't Have to Live with It", *Parade Magazine* (Feb. 19, 1995). Stern also discloses that standard acne medications, when topically applied to rosacea-affected skin, generally irritate the skin and induce rosacea flare-ups. Similarly, agents that dilate blood vessels when ingested, for instance, ethanol (drinking alcohol) and certain medications for high blood pressure, can bring on a rosacea blush when ingested by a person affected with rosacea. Untreated, rosacea can result in swollen veins, scattered lumps, and clusters of pustules on the face. Stern concludes with a brief discussion of treatment of rosacea by ingestion of antibiotics and/or by laser beams directly on the rosacea-affected skin to destroy swollen blood vessels.

A method for the treatment of acne-affected skin is disclosed in U.S. Pat. No. 3,867,522 to Kligman and is of interest. The patent describes a method that requires vigorously rubbing on the acne-affected skin of a composition of about 30% to about 60% by weight of discrete crystals of sodium chloride in a carrier base for about 1 to 2 minutes to cause abrasion and debridement of the affected skin. The crystals of sodium chloride must be of an appropriate particle size, typically from about 200 to about 500 micrometers, to cause the abrasion and debridement. Also, so that the sodium chloride crystals may be frictionally rubbed onto the acne-affected skin, the crystals must be present in a carrier or vehicle, such as stearic acid, glycerylmonostearate, propylene glycol, parahydroxybenzoic acid methylester, or sodium laurylsulfate.

U.S. Pat. No. 3,574,854 to Bossard describes a process for providing a soothing effect on skin. More particularly, the process involves applying to the skin an oil-in-water emulsion that is a cream or paste consisting essentially of marine salt (i.e., sodium chloride accompanied by salts of potassium, magnesium, and calcium), colloidal silica, stearyl alcohol or cetostearyl alcohol, lanoin, polyethylene glycol of molecular weight 400–4000 or glycerol, a coloring agent, and water.

Also, of background interest with respect to use of sodium chloride in the treatment of acne is U.S. Pat. No. 4,443,442 to Skillern. This patent discloses a method for treating acne vulgaris requiring the oral ingestion of a combination composition containing sodium chloride together with an acne-controlling compound chosen from methyclothiazide, polythiazide, or trichlormethazide. At the beginning of the '442 patent to Skillern is a comment that U.S. Pat. No. 4,005,198 to Skillern et al. discloses a method for treating acne vulgaris by oral ingestion of one of these three azide drugs together with the antibiotic, tetracycline. However, as further noted in the '442 patent to Skillern, these three azide drugs, when ingested orally, are also known to have diuretic side effects that result in excretion of sodium chloride during urination. The invention in the '442 patent to Skillern is the discovery that oral ingestion of the combination of sodium chloride with one of these three azide drugs not only enhances the effectiveness of the drug for use in treating acne, but also decreases the incidence of the diuretic side effect. Optionally, an antibiotic, such as tetracycline, is orally taken together with the composition of sodium chloride and azide drug.

Nevertheless, it is still desirable to find a method of treating acne-affected skin and/or rosacea-affected skin topically with sodium chloride that does not require abrasion and debridement of the acne-affected skin (which canexacerbate redness and swelling from irritation of the affected skin) and that does not require oral ingestion of sodium chloride (which can result in nausea, dizziness, and hypertension).

DISCLOSURE OF THE INVENTION

Accordingly, the present invention provides a method for the topical treatment of skin affected with acne, rosacea, or a combination thereof. The method comprises selecting a substantially pure form of sodium chloride and topically applying it to the affected skin by gently gliding it over the affected skin, preferably for about 50 seconds or less, in a manner insufficient to cause abrasion and debridement of the affected skin. It is also preferred that the substantially pure form of sodium chloride consists essentially of about 98% to about 100% by weight of sodium chloride as a solid block. Furthermore, the sodium chloride should be free of a carrier, free of other acne-treatment medicaments, and/or free of other rosacea-treatment medicaments.

To assist in a portion of the sodium chloride from the block leaving the block and forming a film or coating on the affected skin, prior to gliding the block of sodium chloride over the affected skin the affected skin is preferably pre-moistened with water, such as from shaving, bathing, splashing water on the affected skin, and the like. Then, the coating of sodium chloride applied to the affected skin is allowed to dry on the affected skin.

Accordingly, it is an object of the present invention to treat acne-affected skin topically with sodium chloride without any concomitant debridement that is typical of topical acne treatments and that can easily result in red, irritated skin.

It is a further object of the present invention that sodium chloride used in the skin treatment is not orally ingested, and thereby the present invention obviates the risk of nausea, dizziness, or hypertension that can result from oral ingestion of too much sodium chloride.

It is a feature of the present invention that the sodium chloride treatment is also useful in the topical treatment of rosacea, in addition to the topical treatment of acne, which is untrue of standard acne topical medications, which when applied to rosacea-affected skin generally irritate the skin and induce rosacea flare-ups.

Thus, it is an advantage of the present invention that persons who have both acne and rosacea, as well as persons who have only rosacea or who have only acne, may use the inventive method.

Some of the objects, features, and advantages of the invention having been stated above, others will become evident as the description proceeds, when taken in conjunction with the laboratory examples as best described below.

DETAILED DESCRIPTION OF THE INVENTION

As the present invention involves topical treatment, oral ingestion of drugs used in treating acne or rosacea is advantageously avoided. In connection therewith, it is noted that certain of these drugs have troublesome side effects, and others have very dangerous side effects, particularly for females.

For instance, oral ingestion of antibiotics is a typical treatment method for persons affected with acne and/or rosacea. However, a troublesome side effect is that the oral ingestion by females of antibiotics often causes vaginal yeast infections. Moreover, isotretinoin is sold by Roche under the trademark ACCUTANE® for oral ingestion in the treatment of severe acne. However, when orally ingested by a female who is pregnant or shortly thereafter becomes pregnant, isotretinoin can cause dangerous side effects, namely major fetal abnormalities.

Any affected skin area, such as the face, neck, back, or chest of a human, may be topically treated with the method of the present invention. The method may be employed for the treatment of acne, rosacea, or a combination thereof, and is useful for any variation of acne and/or rosacea, whether mild or severe or somewhere in between. Furthermore, the method works similarly well in the treatment of both males and females who have acne and/or rosacea.

More specifically, the inventive method involves topically applying sodium chloride, the chemical formula of which is NaCl, in its substantially pure form to the affected skin. More preferably, a block of substantially pure NaCl should be used. In other words, the block should consist essentially of between about 98% and about 100% by weight NaCl with only trace amounts present of other mineral salts such as magnesium chloride or calcium chloride.

Such pure NaCl naturally occurs as rock salt, also known as the mineral halite. Halite is isometric with cubic habit and cleavage. It is translucent when pure, but may be white, yellow, red, or blue when trace amounts of other minerals are present.

For use in the method of the present invention, the block of NaCl also should be free of any carriers. Typical pharmaceutically acceptable carriers (such as ethanol, glycerol, stearyl alcohol, and glycerylmonostearate, often used to place a medicament in solution form or emulsion form for application) need not be used for the present invention, and preferably, are not used.

Even more preferably, the block of NaCl also should be free of any other medicaments for the topical treatment of acne and/or free of any other medicaments for the topical treatment of rosacea.

Additionally, the block of NaCl should be of appropriate size to be conveniently held in the hand of the user so that it may be gently glided onto the affected skin. A convenient size may range from a cubic shape of about 0.5 inch on a side to a rectangular parallelapiped shape of about 1 inch×1 inch×2 inches, and of course, other convenient shapes, such as cylinders, may be used.

The NaCl, preferably in the form of a block, is topically applied by very gentle gliding motions, such as dabbing motions, circular motions, up and down motions, or zigzag motions, as the NaCl is gently glided over the affected skin. Care must be taken so that gently gliding the NaCl over the affected skin is in a manner insufficient to cause abrasion and debridement of the affected skin.

The gliding should be accomplished in about 50 seconds to about 1 second, and more preferably in about 45 seconds to about 2 seconds. Typically, the gliding will be accomplished in about 30 seconds to about 15 seconds.

After the block of NaCl has been glided over the affected skin, the applied NaCl is left on the skin. Typically, the applied NaCl forms a thin film or coating thereof over the affected skin.

Prior to gliding the block of NaCl on the affected skin, the skin should be pre-moistened with water to assist a portion of the NaCl in leaving the block and staying applied on the affected skin. Then, the applied NaCl will have been wetted, and is left to dry on the skin. The pre-moistening can be accomplished, such as by a male shaving and then after splashing water on the face to remove residual shaving cream, not drying the face. Additionally, the affected skin can be pre-moistened by simply leaving it wet after bathing it. Furthermore, the affected skin can be pre-moistened by simply splashing water thereon.

Application to the affected skin should be at least once during a day, but may be more often depending on the severity of the acne and/or rosacea. Hence, application may be as often as 5 or 6 times during a day, or even more. Typically, for most persons affected with acne and/or rosacea, application once or twice during a day is sufficient.

The application should be repeated for at least 2 weeks on a regular basis, and the acne and/or rosacea will have been alleviated and often eliminated. For severe case of acne and/or rosacea, application on a regular basis should be for at least 2 times during a day and for at least 5 weeks to eliminate the skin condition of acne and/or rosacea.

After elimination of the acne and/or rosacea, application may be once during a day to maintain the skin acne-free and/or rosacea-free.

Laboratory Examples

Example (Testing of Males)

Three male persons, one of whom had rosacea on his face and two of whom each had acne on his face, were treated by the inventive method. A block of mineral pure rock salt that was 98% to 100% sodium chloride was used. It was obtained from S & S Marketing Company, Tempe, Ariz., and F/T Limited, P.O. Box 756, Millbrae Calif. 94030-0756, and had a size of about 3 inches×1 inch×1 inch, and was being sold for use as an underarm deodorant. The testing of the three subjects was as follows:

Test Subject No. 1. This person was a 50-year old male caucasian afflicted with rosacea on his face. He was topically applying an antibiotic, as well as orally ingesting another antibiotic, to treat the rosaoea.

Once per day, after he shaved in the morning, he did not dry his face. Rather, his face was left moistened. Then, he applied NaCl from the block to the rosacea-affected facial areas of the forehead, nose, edges of the cheeks adjacent the nose, and chin on half of his face by very gently gliding the block of sodium chloride in dabbing motions, circular motions, up and down motions, or zigzag motions (the motions being insufficient to cause debridement and abrasion of the affected skin) on the moistened areas for about 15 to about 30 seconds. A thin film of wetted sodium chloride resulted therefrom, and was allowed to remain and to dry on his face. On the other half of his face he continued with the topical application of the antibiotic. He also continued with oral ingestion of the other antibiotic. This once daily application of NaCl to half of his face and the antibiotic to the other half, while orally ingesting the other antibiotic, was continued for 3 weeks. At the end of 1 week, the rosacea was alleviated on the NaCl treated half, and at the end of 2 weeks, the NaCl treated half was clear and the rosacea had been completely eliminated.

At the end of 3 weeks, he stopped both the topical application of one antibiotic and the oral ingestion of the other antibiotic, and proceeded in the following manner with application of NaCl twice during the day for another 2 weeks. Once in the morning after he shaved the NaCl application was repeated in the same manner as noted above but on both sides of his face. Also, once in the evening shortly before going to bed he washed his face, but he did not dry his face. Rather, his face was left moistened, and the NaCl application was repeated on both sides of his face in the same manner as noted above. At the end of 5 weeks, the half of his face that had previously been treated by topical application of an antibiotic was clear and the rosacea had been completely eliminated like the half that had been treated continually with NaCl.

He then stopped the NaCl treatment for 6 days, and the rosacea began to reappear on both sides of his face. Thus, he then returned to the NaCl application on both sides of his face in the same manner as noted above, but only once during the day in the morning after he shaved. After 1 week, the rosacea began to be alleviated. After 2 weeks, his face was again clear and the rosacea completely eliminated. He continued with the once per day application of NaCl and his face remained clear.

Test Subject No. 2. This person was a 14-year old male caucasian afflicted with severe acne on his face.

Once per day, after he washed his face with soap and water and then rinsed with water, he did not dry his face. Rather, his face was left moistened. Then, he applied NaCl from the block to the acne-affected facial areas of the forehead, nose, edges of the cheeks adjacent the nose, and chin, by very gently gliding the block in dabbing motions, circular motions, up and down motions, or zigzag motions (the motions being insufficient to cause debridement and abrasion of the affected skin) on the moistened areas for about 15 to about 30 seconds. A thin film of wetted sodium chloride resulted therefrom, and was allowed to remain and to dry on his face.

This once daily application was continued for 5 weeks. At the end of 2 weeks, the acne began to be alleviated. At the end of 5 weeks, his face was clear and the acne completely eliminated. He continued with the once per day application of NaCl and his face remained clear.

Test Subject No. 3. This person was a 20-year old male caucasian afflicted with extremely severe acne on his face.

Once per day, after he shaved in the morning, he did not dry his face. Rather, his face was left moistened. Then, he applied NaCl from the sodium chloride block to the acne-affected facial areas of the forehead, nose, edges of the cheeks adjacent the nose, and chin, by very gently gliding the block in dabbing motions, circular motions, up and down motions, or zigzag motions (the motions being insufficient to cause debridement and abrasion of the affected skin) on the moistened areas for about 15 to about 30 seconds. A thin film of wetted sodium chloride resulted therefrom, and was allowed to remain and to dry on his face.

This once daily application was continued for 2 weeks. At the end of 1 week, the acne began to be alleviated. At the end of 2 weeks, his face was clear and the acne substantially eliminated. He stopped the application of NaCl and instead began using a cosmetic cover up on his face. Shortly thereafter, the acne returned with the extreme severity that he had prior to his initiation of the NaCl treatment to his face.

It is noted that for each of the 3 test subjects, within a few minutes of the NaCl having dried, a therapeutic effect was observed in that the redness of inflamed areas (typically occurring from washing, shaving and the like of affected skin) diminished and was hardly noticeable, even with the first NaCl treatment. On the other hand, previous to NaCl treatment, this redness would last about half of an hour before subsiding.

Example II (Testing of Females)

The method may be repeated in the same manner of application as with the second male test subject noted above, either once per day, twice per day, or more times, depending on the severity of the acne and/or rosacea, but instead with female persons having rosacea-affected skin, acne-affected skin, or a combination thereof, and the results should be the same.

It will be understood that various details of the invention may be changed without further departing from the scope of the invention. Furthermore, the foregoing description is for the purpose of illustration only, and not for the purpose of limitation—the invention being defined by the claims.

What is claimed is:

1. A method for the topical treatment of skin affected with rosacea consisting essentially of the steps of:
   (a) selecting a substantially pure form of sodium chloride consisting essentially of a solid block containing about 98% to about 100% by weight sodium chloride;
   (b) applying the solid block of sodium chloride by gently gliding it over the affected skin in a manner insufficient to cause abrasion and debridement of the affected skin; and
   (c) allowing the applied sodium chloride to remain on the affected skin.

2. The method of claim 1, wherein the block of sodium chloride is free of other mineral salts except for trace amounts thereof.

3. The method of claim 2, wherein the block of sodium chloride is free of a carrier.

4. The method of claim 2, wherein the block of sodium chloride is free of other medicaments for topical treatment of rosacea.

5. The method of claim 1, wherein gliding the sodium chloride over the affected skin is accomplished by gentle rubbing motions selected from the group consisting of dabbing motions, circular motions, up and down motions, zigzag motions, and combinations thereof.

6. The method of claim 1, wherein gliding the sodium chloride over the affected skin is accomplished in about 50 seconds to about 1 second.

7. The method of claim 6, wherein gliding the sodium chloride over the affected skin is accomplished in about 45 seconds to about 2 seconds.

8. The method of claim 1, wherein the applied sodium chloride forms a film on the affected skin.

9. The method of claim 1, wherein prior to gliding the sodium chloride over the affected skin in step (b), the affected skin is pre-moistened with water, and then, gliding the sodium chloride over the affected skin results in the sodium chloride becoming wet, and then in step (c), the wetted applied sodium chloride remaining on the affected skin is allowed to dry on the affected skin.

10. The method of claim 1, wherein steps (a), (b), and (c) are accomplished at least once per day.

* * * * *